United States Patent
Martinussen et al.

(10) Patent No.: US 8,658,357 B2
(45) Date of Patent: Feb. 25, 2014

(54) OROTATE TRANSPORTER ENCODING MARKER GENES

(75) Inventors: Jan Martinussen, Bagsvaerd (DK); Els Marie Celine Defoor, Niva (DK)

(73) Assignee: Novozymes A/S, Bagsvaerd (DK)

( * ) Notice: Subject to any disclaimer, the term of this patent is extended or adjusted under 35 U.S.C. 154(b) by 10 days.

(21) Appl. No.: 12/688,303

(22) Filed: Jan. 15, 2010

(65) Prior Publication Data

US 2010/0120052 A1    May 13, 2010

Related U.S. Application Data

(62) Division of application No. 10/586,932, filed as application No. PCT/DK2005/000092 on Feb. 11, 2005, now abandoned.

(60) Provisional application No. 60/545,774, filed on Feb. 19, 2004.

(30) Foreign Application Priority Data

Feb. 13, 2004  (DK) ................................ 2004 00227

(51) Int. Cl.
    *C12Q 1/68*    (2006.01)
(52) U.S. Cl.
    USPC ............................... 435/6.1; 435/34; 435/440
(58) Field of Classification Search
    None
    See application file for complete search history.

(56) References Cited

FOREIGN PATENT DOCUMENTS

FR    2807446        10/2001
WO    WO 01/77334    10/2001

OTHER PUBLICATIONS

Jonuscheit et al, Molecular Microbiology, vol. 48 (5), pp. 1241-1252 (2003).
Tamakoshi et al, Journal of Bacteriology, vol. 179, No. 15 (1997).
Baker et al, Journal of Baceriology, vol. 178, No. 24 pp. 7099-7105 (1996).
Bai Xiyuan et al., "The *URA5* Gene Encoding Orotate-phosphoribosyl Transferase of the Yeast *Kluyveromyces lactis*: Cloning, Sequencing and Use as a Selectable Marker", Yeast, vol. 15, No. 13, pp. 1393-1398 (1999).
Martinussen et al., "The orotate transporter encoded by oroP from *Lactococcus lactis* is required for orotate utilization and has utility as a food-grade selectable marker", Microbiology, vol. 153, pp. 3645-3659.

*Primary Examiner* — Patricia A Duffy
(74) *Attorney, Agent, or Firm* — Michael W. Krenicky; Eric J. Fechter

(57) ABSTRACT

A recombinant marker gene encoding an orotate transporter polypeptide comprising an amino acid sequence at least 60% identical to SEQ ID NO: 2, a polynucleotide construct comprising at least one copy of the recombinant marker gene, a cell comprising at least one exogenous copy of the marker gene, and a method of selecting or identifying a cell comprising at least one copy of the recombinant marker gene, and/or selecting or identifying a cell which has been cured of the recombinant marker gene.

22 Claims, 1 Drawing Sheet

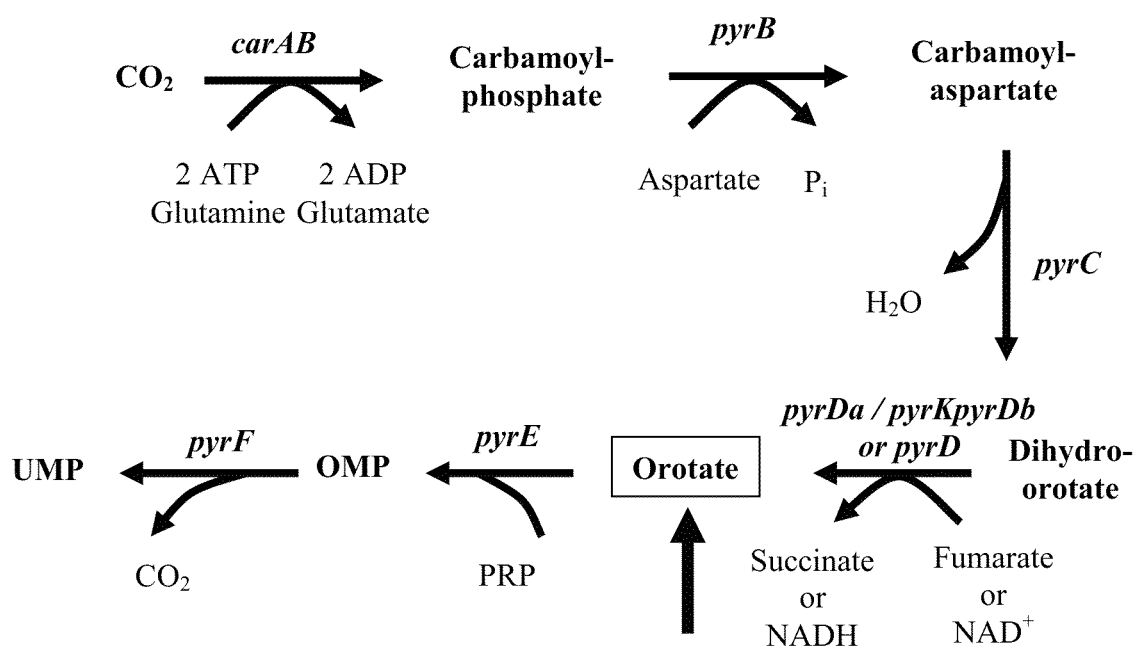

SEQUENCE LISTING

<160> NUMBER OF SEQ ID NOS: 22

<210> SEQ ID NO 1
<211> LENGTH: 921
<212> TYPE: DNA
<213> ORGANISM: Lactococcus lactis
<220> FEATURE:
<221> NAME/KEY: CDS
<222> LOCATION: (1)..(921)

<223> OTHER INFORMATION: Orotate transporter encoding ORF

<400> SEQUENCE: 1

```
atg tat att tac cta gct ttt gca tta gtt ggc ggt ttt tta ctt gct      48
Met Tyr Ile Tyr Leu Ala Phe Ala Leu Val Gly Gly Phe Leu Leu Ala
1               5                   10                  15 aat caa aat cca atc aat gcg gat tta cga aaa att gtt ggc tca cca      96
Asn Gln Asn Pro Ile Asn Ala Asp Leu Arg Lys Ile Val Gly Ser Pro
            20                  25                  30 ttt ttg gcc tct gga att tcc aac ttt gtt ggt tcg att ttt tta gga     144
Phe Leu Ala Ser Gly Ile Ser Asn Phe Val Gly Ser Ile Phe Leu Gly
        35                  40                  45 att atc act tta gtg acc agt caa aca ctt ttt cct agt ttt caa ttt     192
Ile Ile Thr Leu Val Thr Ser Gln Thr Leu Phe Pro Ser Phe Gln Phe
50                  55                  60 gtt ggc tca cac cca gta tgg ata tgg att ggt ggg gtt ctt ggt ggg     240
Val Gly Ser His Pro Val Trp Ile Trp Ile Gly Gly Val Leu Gly Gly
65                  70                  75                  80 att ttt cta aca tct aat gtt tta ctt ttc cca aga tta gga gct gtc     288
Ile Phe Leu Thr Ser Asn Val Leu Leu Phe Pro Arg Leu Gly Ala Val
                85                  90                  95 caa acg gtg att tta cct att ttg ggt cga ata ttg atg ggg aca ctt     336
Gln Thr Val Ile Leu Pro Ile Leu Gly Arg Ile Leu Met Gly Thr Leu
            100                 105                 110 att gat tca ttt ggc tgg ttt cat gcc atg caa ctt ccg atg act ctg     384
Ile Asp Ser Phe Gly Trp Phe His Ala Met Gln Leu Pro Met Thr Leu
        115                 120                 125 atg cgc ttt ttg gga gtt atc att act tta gct ggg gtt att gtc gcg     432
Met Arg Phe Leu Gly Val Ile Ile Thr Leu Ala Gly Val Ile Val Ala
    130                 135                 140 gtt gtt ctt cct aat tta aaa gaa aaa gaa gca gaa acg cac caa act     480
Val Val Leu Pro Asn Leu Lys Glu Lys Glu Ala Glu Thr His Gln Thr
145                 150                 155                 160 aac tta cta ggc tgg cga att tgg gcg gtc atc gtt ggg gca atg tcg     528
Asn Leu Leu Gly Trp Arg Ile Trp Ala Val Ile Val Gly Ala Met Ser
                165                 170                 175 gct gct caa caa gca att aat ggc aga ttg gga gtt tta ctt gaa aac     576
Ala Ala Gln Gln Ala Ile Asn Gly Arg Leu Gly Val Leu Leu Glu Asn
            180                 185                 190 act gca caa gca acc ttt gtt tcg ttc ttc att gga ttt tta gct att     624
Thr Ala Gln Ala Thr Phe Val Ser Phe Phe Ile Gly Phe Leu Ala Ile
        195                 200                 205 ttt atc gtg tct ctt ttt att gac cgc cgt ttg cca aaa att tca gaa     672
Phe Ile Val Ser Leu Phe Ile Asp Arg Arg Leu Pro Lys Ile Ser Glu
    210                 215                 220 tta aaa aaa gca aaa cct tgg aat gga att ggt gga ttt tta gga gcc     720
Leu Lys Lys Ala Lys Pro Trp Asn Gly Ile Gly Gly Phe Leu Gly Ala
225                 230                 235                 240 tca atc gtt ttt gca aca gtc gtt gct gtt ccg caa att ggt gca ggg     768
Ser Ile Val Phe Ala Thr Val Val Ala Val Pro Gln Ile Gly Ala Gly
                245                 250                 255 ctg aca att atg atg ggc ttg att gga caa att tta ggc agt atg ttg     816
Leu Thr Ile Met Met Gly Leu Ile Gly Gln Ile Leu Gly Ser Met Leu
            260                 265                 270 gtt caa caa ttt ggt tgg tgg cgc tca agt aaa tat ggc att caa att     864
Val Gln Gln Phe Gly Trp Trp Arg Ser Ser Lys Tyr Gly Ile Gln Ile
        275                 280                 285 tgg caa att gtt ggg att cta att atg ctg acc gga ata ata ttc att     912
Trp Gln Ile Val Gly Ile Leu Ile Met Leu Thr Gly Ile Ile Phe Ile
    290                 295                 300
```

```
aaa ttt tta                                                          921
Lys Phe Leu
305
```

<210> SEQ ID NO 2
<211> LENGTH: 307
<212> TYPE: PRT
<213> ORGANISM: Lactococcus lactis

<400> SEQUENCE: 2

```
Met Tyr Ile Tyr Leu Ala Phe Ala Leu Val Gly Gly Phe Leu Leu Ala
1               5                   10                  15

Asn Gln Asn Pro Ile Asn Ala Asp Leu Arg Lys Ile Val Gly Ser Pro
            20                  25                  30

Phe Leu Ala Ser Gly Ile Ser Asn Phe Val Gly Ser Ile Phe Leu Gly
        35                  40                  45

Ile Ile Thr Leu Val Thr Ser Gln Thr Leu Phe Pro Ser Phe Gln Phe
    50                  55                  60

Val Gly Ser His Pro Val Trp Ile Trp Ile Gly Val Leu Gly Gly
65                  70                  75                  80

Ile Phe Leu Thr Ser Asn Val Leu Leu Phe Pro Arg Leu Gly Ala Val
                85                  90                  95

Gln Thr Val Ile Leu Pro Ile Leu Gly Arg Ile Leu Met Gly Thr Leu
            100                 105                 110

Ile Asp Ser Phe Gly Trp Phe His Ala Met Gln Leu Pro Met Thr Leu
        115                 120                 125

Met Arg Phe Leu Gly Val Ile Ile Thr Leu Ala Gly Val Ile Val Ala
    130                 135                 140

Val Val Leu Pro Asn Leu Lys Glu Lys Glu Ala Glu Thr His Gln Thr
145                 150                 155                 160

Asn Leu Leu Gly Trp Arg Ile Trp Ala Val Ile Val Gly Ala Met Ser
                165                 170                 175

Ala Ala Gln Gln Ala Ile Asn Gly Arg Leu Gly Val Leu Leu Glu Asn
            180                 185                 190

Thr Ala Gln Ala Thr Phe Val Ser Phe Phe Ile Gly Phe Leu Ala Ile
        195                 200                 205

Phe Ile Val Ser Leu Phe Ile Asp Arg Arg Leu Pro Lys Ile Ser Glu
    210                 215                 220

Leu Lys Lys Ala Lys Pro Trp Asn Gly Ile Gly Phe Leu Gly Ala
225                 230                 235                 240

Ser Ile Val Phe Ala Thr Val Val Ala Val Pro Gln Ile Gly Ala Gly
                245                 250                 255

Leu Thr Ile Met Met Gly Leu Ile Gly Gln Ile Leu Gly Ser Met Leu
            260                 265                 270

Val Gln Gln Phe Gly Trp Trp Arg Ser Ser Lys Tyr Gly Ile Gln Ile
        275                 280                 285

Trp Gln Ile Val Gly Ile Leu Ile Met Leu Thr Gly Ile Ile Phe Ile
    290                 295                 300

Lys Phe Leu
305
```

<210> SEQ ID NO 3
<211> LENGTH: 25
<212> TYPE: DNA
<213> ORGANISM: Artificial sequence
<220> FEATURE:
<223> OTHER INFORMATION: Primer pyrDaBamHI

```
<400> SEQUENCE: 3
cgggatccat gaccgcacca acagc                                    25

<210> SEQ ID NO 4
<211> LENGTH: 28
<212> TYPE: DNA
<213> ORGANISM: Artificial sequence
<220> FEATURE:
<223> OTHER INFORMATION: Primer pyrDaNcoI

<400> SEQUENCE: 4
catgccatgg ccaaatccat ctttaggc                                 28

<210> SEQ ID NO 5
<211> LENGTH: 29
<212> TYPE: DNA
<213> ORGANISM: Artificial sequence
<220> FEATURE:
<223> OTHER INFORMATION: Primer pyrDaHindIII

<400> SEQUENCE: 5
cgtgaagctt gacaaaatag gctgacctc                                29

<210> SEQ ID NO 6
<211> LENGTH: 20
<212> TYPE: DNA
<213> ORGANISM: Artificial sequence
<220> FEATURE:
<223> OTHER INFORMATION: Primer PSA17

<400> SEQUENCE: 6
atgccgcctc atcatttgac                                          20

<210> SEQ ID NO 7
<211> LENGTH: 20
<212> TYPE: DNA
<213> ORGANISM: Artificial sequence
<220> FEATURE:
<223> OTHER INFORMATION: Primer PSA20

<400> SEQUENCE: 7
atatcatctc ttttggtaat                                          20

<210> SEQ ID NO 8
<211> LENGTH: 28
<212> TYPE: DNA
<213> ORGANISM: Artificial sequence
<220> FEATURE:
<223> OTHER INFORMATION: Primer pyrDbIF

<400> SEQUENCE: 8
cggaagatct gatgatgaca gttgtcag                                 28

<210> SEQ ID NO 9
<211> LENGTH: 46
<212> TYPE: DNA
<213> ORGANISM: Artificial sequence
<220> FEATURE:
<223> OTHER INFORMATION: Primer pyrDbIR

<400> SEQUENCE: 9
ctgtactggt ccataagctc ggatccacca aaacaacctg acgctg              46

<210> SEQ ID NO 10
<211> LENGTH: 46
<212> TYPE: DNA
```

```
<213> ORGANISM: Artificial sequence
<220> FEATURE:
<223> OTHER INFORMATION: Primer pyrDbIIF

<400> SEQUENCE: 10
cagcgtcagg ttgttttggt ggatccgagc ttatggacca gtacag         46

<210> SEQ ID NO 11
<211> LENGTH: 28
<212> TYPE: DNA
<213> ORGANISM: Artificial sequence
<220> FEATURE:
<223> OTHER INFORMATION: Primer pyrDbIIR

<400> SEQUENCE: 11
tcggagatct atccaaggac aagtgcag                              28

<210> SEQ ID NO 12
<211> LENGTH: 17
<212> TYPE: DNA
<213> ORGANISM: Artificial sequence
<220> FEATURE:
<223> OTHER INFORMATION: Primer pyrDbseq1

<400> SEQUENCE: 12
tggtggaatt ggggttc                                          17

<210> SEQ ID NO 13
<211> LENGTH: 17
<212> TYPE: DNA
<213> ORGANISM: Artificial sequence
<220> FEATURE:
<223> OTHER INFORMATION: Primer pyrDbseq2

<400> SEQUENCE: 13
caaggtctgc gaagatg                                          17

<210> SEQ ID NO 14
<211> LENGTH: 17
<212> TYPE: DNA
<213> ORGANISM: Artificial sequence
<220> FEATURE:
<223> OTHER INFORMATION: Primer pyrDbseq3

<400> SEQUENCE: 14
attgacagaa ctgccag                                          17

<210> SEQ ID NO 15
<211> LENGTH: 18
<212> TYPE: DNA
<213> ORGANISM: Artificial sequence
<220> FEATURE:
<223> OTHER INFORMATION: Primer DBORO2

<400> SEQUENCE: 15
acttatcgtc cggacttg                                         18

<210> SEQ ID NO 16
<211> LENGTH: 18
<212> TYPE: DNA
<213> ORGANISM: Artificial sequence
<220> FEATURE:
<223> OTHER INFORMATION: Primer DBORO8

<400> SEQUENCE: 16
cattagaaag cgcacgac                                         18
```

```
<210> SEQ ID NO 17
<211> LENGTH: 26
<212> TYPE: DNA
<213> ORGANISM: Artificial sequence
<220> FEATURE:
<223> OTHER INFORMATION: Primer DBORO22BamHI

<400> SEQUENCE: 17
caggatccta ctgacagact tgtcag                                      26

<210> SEQ ID NO 18
<211> LENGTH: 26
<212> TYPE: DNA
<213> ORGANISM: Artificial sequence
<220> FEATURE:
<223> OTHER INFORMATION: Primer DBORO23EcoRI

<400> SEQUENCE: 18
gagaattctg attcggacaa ggcttc                                      26

<210> SEQ ID NO 19
<211> LENGTH: 26
<212> TYPE: DNA
<213> ORGANISM: Artificial sequence
<220> FEATURE:
<223> OTHER INFORMATION: Primer DBORO24EcoRI

<400> SEQUENCE: 19
gagaattcaa agtcgttcgc ctcaag                                      26

<210> SEQ ID NO 20
<211> LENGTH: 18
<212> TYPE: DNA
<213> ORGANISM: Artificial sequence
<220> FEATURE:
<223> OTHER INFORMATION: Primer DBORO4

<400> SEQUENCE: 20
ttcacgctca ctaccttc                                               18

<210> SEQ ID NO 21
<211> LENGTH: 23
<212> TYPE: DNA
<213> ORGANISM: Artificial sequence
<220> FEATURE:
<223> OTHER INFORMATION: Primer DBORO20

<400> SEQUENCE: 21
ggctcaccat ttttggcctc tgg                                         23

<210> SEQ ID NO 22
<211> LENGTH: 17
<212> TYPE: DNA
<213> ORGANISM: Artificial sequence
<220> FEATURE:
<223> OTHER INFORMATION: Primer 268neo

<400> SEQUENCE: 22
ctcattccct gatctcg                                                17
```

US 8,658,357 B2

OROTATE TRANSPORTER ENCODING MARKER GENES

CROSS-REFERENCE TO RELATED APPLICATIONS

This application is a divisional of U.S. patent application Ser. No. 10/586,932 filed Jul. 21, 2006 which is a 35 U.S.C. 371 national application of PCT/DK2005/000092 filed 11 Feb. 2005, which claims priority or the benefit under 35 U.S.C. 119 of Danish application no. PA 2004 00227 filed 13 Feb. 2004, and U.S. provisional application No. 60/545,774, filed 19 Feb. 2004, the contents of which are fully incorporated herein by reference

FIELD OF THE INVENTION

The present invention relates to a pioneering new class of orotate transporter polypeptide encoding marker genes. One orotate transporter of the invention is derived from a *Lactococcus lactis* strain, and is encoded by the ysbC gene. It is demonstrated herein that the orotate transporter gene is suitable to be used as a versatile non-antibiotic marker gene, both in selection, counter-selection, screening, and bi-directional selection protocols.

BACKGROUND

A putative gene, denoted ysbC, was previously identified by genome sequencing of a *Lactococcus lactis* strain, but the gene was not annotated, and no function of the predicted encoded polypeptide was identified (WO 200177334, Bolotin et al., 2001, The Complete Genome Sequence of the Lactic Acid Bacterium *Lactococcus lactis* ssp. *Lactis* IL1403, Genome Res. 11:731). The amino acid sequence of the predicted YsbC protein is available from the database GeneSeqP, accession number: ABB55104.

There is growing concern in the public, as well as in the scientific communities, about the use of antibiotics in molecular biology. In particular, there is concern about the cultivation of recombinant cells carrying antibiotic genetic markers, mostly due to the perceived potential risk for lateral transfer of such markers into nature. It is therefore of interest to identify new non-antibiotic marker genes to substitute the classical antibiotic resistance encoding selection, counter-selection, screening, and bi-directional selection markers in molecular biology.

The present invention relates to an orotate transporter polypeptide derived from a *Lactococcus lactis* strain. The orotate transporter is encoded by the ysbC gene, an open reading frame, which was predicted but not annotated in an earlier genome sequencing project.

A search in the public databases for any polypeptides having amino acid sequence homology to the orotate transporter of the present invention, revealed that the closest polypeptide had less than 35% sequence identity, and it was completely unrelated to the orotate transporter of the present invention. Consequently, the ysbC-encoded orotate transporter represents a completely pioneering new class of molecules.

The newly identified orotate transporter was shown to be functional in both Gram-positive and Gram-negative bacterial cells, and it was shown that ysbC is ideally suited as a versatile non-antibiotic marker gene, suitable for use in selection, counter-selection, screening, and bi-directional selection protocols, as exemplified below.

DESCRIPTION OF FIGURES

FIG. 1. Schematic representation of the de novo de biosynthetic pathway of pyrimidines leading to the formation of uracil-mono-phosphate (UMP). Usually, the fourth step in the pathway is catalysed by a single pyrD gene product, but in *Lactococcus lactis* two pyrD genes, pyrDa and pyrDb, are found both coding for a functional biosynthetic dihydroorotate dehydrogenase. The genes coding for the other enzymatic activities are: carAB (carbamoylphosphate synthetase); pyrB (aspartate carbamoyl transferase); pyrC (dihydroorotase); pyrD (dihydroorotate dehydrogenase); pyrDa (dihydroorotate dehydrogenase A); pyrDKpyrDb (dihydroorotate dehydrogenase B); pyrE (orotate phosphoribosyl transferase); pyrF (OMP decarboxylase). PRP designates 5-phosphoribosyl-alpha-1-pyrophosphate.

SUMMARY OF THE INVENTION

A problem to be solved by the present invention is to provide a non-antibiotic recombinant marker of a versatile nature, suitable for substituting classical antibiotic-resistance encoding genes in molecular biology procedures, and to provide methods for selecting and/or identifying cells comprising at least one copy of the recombinant non-antibiotic marker, as well as cells cured of said marker.

The invention provides a pioneering new class of very versatile orotate transporter molecules as a solution; genes encoding versatile orotate transporters are highly suitable as non-antibiotic markers. Based on this invention, and on the sequence information, it is a straightforward matter for the skilled person to isolate numerous related molecules with orotate transporter activity from any cell harbouring a related gene.

Accordingly, in a first aspect, the invention relates to a recombinant marker gene encoding an orotate transporter polypeptide comprising an amino acid sequence at least 60% identical to SEQ ID NO: 2, preferably at least 65%, or more preferably at least 70%, 75%, 80%, 85%, 90%, 95%, 97%, or most preferably at least 99% identical to SEQ ID NO: 2; or a recombinant marker gene encoding an orotate transporter polypeptide, said marker gene comprising a polynucleotide sequence at least 60% identical to SEQ ID NO: 1, preferably at least 65%, or more preferably at least 70%, 75%, 80%, 85%, 90%, 95%, 97%, or most preferably at least 99% identical to SEQ ID NO: 1; or a recombinant marker gene encoding an orotate transporter polypeptide, said marker gene comprising a polynucleotide sequence which hybridizes with the sequence shown in SEQ ID NO:1, under very low stringency conditions, preferably low stringency, more preferably medium stringency, even more preferably under medium-high stringency, still more preferably under high stringency, and most preferably under very high stringency conditions.

In a second aspect, the invention relates to a polynucleotide construct comprising at least one recombinant marker gene encoding an orotate transporter polypeptide comprising an amino acid sequence at least 60% identical to SEQ ID NO: 2, preferably at least 65%, or more preferably at least 70%, 75%, 80%, 85%, 90%, 95%, 97%, or most preferably at least 99% identical to SEQ ID NO: 2; or a polynucleotide construct comprising at least one recombinant marker gene encoding an orotate transporter polypeptide, said marker gene comprising a polynucleotide sequence at least 60% identical to SEQ ID NO: 1, preferably at least 65%, or more preferably at least 70%, 75%, 80%, 85%, 90%, 95%, 97%, or most preferably at least 99% identical to SEQ ID NO: 1; or a polynucleotide construct comprising at least one recombinant marker gene encoding an orotate transporter polypeptide, said marker gene comprising a polynucleotide sequence, which hybridizes with the sequence shown in SEQ ID NO:1, under very low stringency conditions, preferably low stringency, more preferably medium stringency, even more preferably under medium-high stringency, still more preferably under high stringency, and most preferably under very high stringency conditions.

In a third aspect, the invention relates to a cell comprising at least one exogenous marker gene encoding an orotate transporter polypeptide comprising an amino acid sequence at least 60% identical to SEQ ID NO: 2, preferably at least 65%, or more preferably at least 70%, 75%, 80%, 85%, 90%, 95%, 97%, or most preferably at least 99% identical to SEQ ID NO: 2; or at least one exogenous marker gene encoding an orotate transporter polypeptide, said marker gene comprising a polynucleotide sequence at least 60% identical to SEQ ID NO: 1, preferably at least 65%, or more preferably at least 70%, 75%, 80%, 85%, 90%, 95%, 97%, or most preferably at least 99% identical to SEQ ID NO: 1; or at least one exogenous marker gene encoding an orotate transporter polypeptide, said marker gene comprising a polynucleotide sequence which hybridizes with the sequence shown in SEQ ID NO:1, under very low stringency conditions, preferably low stringency, more preferably medium stringency, even more preferably under medium-high stringency, still more preferably under high stringency, and most preferably under very high stringency conditions.

A final aspect of the invention relates to a method of selecting or identifying a cell comprising at least one copy of a recombinant marker gene, and/or selecting or identifying a cell which has been cured of the recombinant marker gene, wherein said marker gene encodes an orotate transporter polypeptide comprising an amino acid sequence at least 60% identical to SEQ ID NO: 2, preferably at least 65%, or more preferably at least 70%, 75%, 80%, 85%, 90%, 95%, 97%, or most preferably at least 99% identical to SEQ ID NO: 2; or encodes an orotate transporter polypeptide, and comprises a polynucleotide sequence at least 60% identical to SEQ ID NO: 1, preferably at least 65%, or more preferably at least 70%, 75%, 80%, 85%, 90%, 95%, 97%, or most preferably at least 99% identical to SEQ ID NO: 1; or encodes an orotate transporter polypeptide, and comprises a polynucleotide sequence which hybridizes with the sequence shown in SEQ ID NO:1, under very low stringency conditions, preferably low stringency, more preferably medium stringency, even more preferably under medium-high stringency, still more preferably under high stringency, and most preferably under very high stringency conditions, and said method comprising the step of using the marker gene as a selection marker, a screening marker, a counter-selection marker, or a bi-directional marker, under suitable conditions, whereby the cell is selected or identified.

DEFINITIONS

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989") DNA Cloning: A Practical Approach, Volumes I and II/D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984).

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

A "nucleic acid molecule" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "recombinant marker gene" is a polynucleotide marker, which has undergone a molecular biological manipulation, and which is comprised in an isolated polynucleotide construct, which may be circular, linear, or multimerized, wherein the marker gene is sufficient to serve as a basis for selecting or screening for its own presence, or absence, within a host cell, when the construct has been introduced into a host cell, or when it has been cured from a host cell, respectively. Classical recombinant marker genes include the genes coding for resistance to various antibiotics.

Hybridization

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

For purposes of the present invention, hybridization indicates that the nucleotide sequence hybridizes to a labeled polynucleotide probe which hybridizes to the nucleotide sequence shown in SEQ ID NO:1 under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of a fragment of at least 15 nucleotides of SEQ ID NO:1. In another interesting embodiment, the polynucleotide probe is a fragment of at least 15 nucleotides of the complementary strand of any nucleotide sequence which encodes the polypeptide of SEQ ID NO:2. In a further interesting embodiment, the polynucleotide probe is the complementary strand of SEQ ID NO:1. In a still further interesting embodiment, the polynucleotide probe is the complementary strand of the mature polypeptide coding region of SEQ ID NO:1.

For long probes of at least 100 nucleotides in length, very low to very high stringency conditions are defined as prehybridization and hybridization at 42° C. in 5×SSPE, 1.0% SDS, 5×Denhardt's solution, 100 micro-g/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated Tm using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated Tm.

Auxotrophy

In the present context the term "auxotrophy" has the generally recognized meaning, i.e. the inability of an organism to synthesize a particular organic compound required for its growth (IUPAC Compendium of Chemical Terminology, 2$^{nd}$ Edition, 1997. 1992, 64, 147).

Sequence Homology and Alignment

For the purposes of the present invention, the homology between two amino acid sequences or between two nucleotide sequences is described by the parameter "identity". The degree of identity between two amino acid sequences is determined by the alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Multiple alignments of protein sequences may be made using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680). Multiple alignment of DNA sequences may be done using the protein alignment as a template, replacing the amino acids with the corresponding codon from the DNA sequence.

Allelic Variant

In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Nucleic Acid Construct

The present invention also relates to nucleic acid constructs comprising a nucleotide sequence of the present invention operably linked to one or more control sequences that direct the expression of the coding sequence in a suitable host cell under conditions compatible with the control sequences.

A nucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention. Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Isolation of Related Orotate Transporters

The nucleotide sequence of SEQ ID NO:1 or a subsequence thereof, as well as the amino acid sequence of SEQ ID NO:2 or a fragment thereof, may be used to design a polynucleotide probe to identify and clone DNA encoding polypeptides having orotate transporter activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15 nucleotides in length, preferably at least 25 nucleotides in length, more preferably at least 35 nucleotides in length, such as at least 70 nucleotides in length. It is, however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labeled for detecting the corresponding gene (for example, with 32P, 3H, 35S, biotin, or avidin).

Thus, a genomic DNA or cDNA library prepared from such other organisms may be screened for DNA which hybridizes with the probes described above and which encodes a polypeptide having orotate transporter activity. Genomic or other DNA from such other organisms may be separated by agarose or polyacrylamide gel electrophoresis, or other separation techniques. DNA from the libraries or the separated DNA may be transferred to, and immobilized, on nitrocellulose or other suitable carrier materials. In order to identify a clone or DNA which is homologous with SEQ ID NO:1 the carrier material with the immobilized DNA is used in a Southern blot.

For purposes of the present invention, hybridization indicates that the nucleotide sequence hybridizes to a labeled polynucleotide probe which hybridizes to the nucleotide sequence shown in SEQ ID NO:1 under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

A polypeptide of the present invention may be obtained from microorganisms of any genus. For purposes of the present invention, the term "obtained from" as used herein shall mean that the polypeptide encoded by the nucleotide sequence is produced by a cell in which the nucleotide sequence is naturally present or into which the nucleotide sequence has been inserted.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide.

In an interesting embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another interesting embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide. It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleotide sequence may then be derived by similarly screening a genomic or cDNA library of another microorganism. Once a nucleotide sequence encoding a polypeptide has been detected with the probe(s), the sequence may be isolated or cloned by utilizing techniques which are known to those of ordinary skill in the art (see, e.g., Sambrook et al., 1989, supra).

The techniques used to isolate or clone a nucleotide sequence encoding a polypeptide are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other amplification procedures such as ligase chain reaction (LCR), ligated activated transcription (LAT) and nucleotide sequence-based amplification (NASBA) may be used.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

Polypeptides encoded by nucleotide sequences of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Variant Molecules

Modification of a nucleotide sequence encoding a polypeptide of the present invention may be necessary for the synthesis of a polypeptide, which comprises an amino acid sequence that has at least one substitution, deletion and/or insertion as compared to SEQ ID NO:2. These artificial variants may differ in some engineered way from the polypeptide isolated from its native source, e.g., variants that differ in specific activity, thermostability, pH optimum, or the like. It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for [enzyme] activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme. The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, Protein Expression and Purification 2: 95-107.

Expression Vectors

The present invention also relates to recombinant expression vectors comprising the nucleic acid construct of the invention. The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to a recombinant host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

In an even more preferred embodiment, the yeast host cell is a *Candida*, *Hansenula*, *Kluyveromyces*, *Pichia*, *Saccharomyces*, *Schizosaccharomyces*, or *Yarrowia* cell.

In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to,

*Acremonium, Aspergillus, Fusarium, Humicola, Mucor, Myceliophthora, Neurospora, Penicillium, Thielavia, Tolypocladium*, or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

DETAILED DESCRIPTION OF THE INVENTION

The first aspect relates to a recombinant marker gene encoding an orotate transporter polypeptide comprising an amino acid sequence at least 60% identical to SEQ ID NO: 2. With the pioneering identification orotate transporter activity of the ysbC encoded polypeptide has been identified, as disclosed herein, and there is full access to the ysbC sequence, it is a straightforward and trivial matter to isolate corresponding ysbC homologues from any cell harbouring a related orotate transporter encoding gene.

Traditionally, molecular biologists have discerned between selective markers, and screening markers. A selective marker typically allow only those cells wherein the marker is present to grow under certain selective conditions, whereas a screening marker conversely only inhibits the growth of those cells wherein the marker is present, thus clearly identifying them. When molecular biologists are interested in the removal of a marker from a host cell, typically either by a crossing-out event from the chromosome, or by the curing of a plasmid from the cytoplasm, then the term "counter-selection" is often used. Counter-selection may be based on a selective method, or on a screening method. When a marker has properties allowing the selection or screening for a first introduction into a host cell, and then a selection of screening for the subsequent removal from the host cell, depending on the conditions, the marker is typically referred to as a "bi-directional selection marker".

Accordingly, a preferred embodiment of the invention relates to the marker gene of the first aspect, which is a selection marker, a screening marker, a counter-selection marker, and/or a bi-directional selection marker.

One very versatile orotate transporter encoding marker is identified in the present application, and the versatility is based in part on that the marker is capable of transporting not only orotate into its host cell, but also an orotate analogue, 5-fluoroorotate (FOA), which inhibits growth of its host cell, as demonstrated in the non-limiting examples below.

So, in a preferred embodiment, the invention relates to the marker gene of the first aspect, wherein the encoded orotate transporter polypeptide also transports one or more orotate analogues, preferably the orotate analogue 5-fluoroorotate.

In order to achieve higher or lower expression of the marker gene of the invention, the inventors suggest adjusting the promoter-strength by using at least one heterologous and/or artificial promoter. How to adjust promoter-strength was disclosed in, e.g., WO 93/10249, and in WO 98/07846 (both Novozymes NS), both of which are incorporated herein in their entirety by reference. Methods for increasing promoter activity by having multiple promoters in-line, optionally coupled with mRNA stabilizing sequences, were disclosed in WO 99/43835 (Novozymes NS), which is also incorporated herein in its entirety by reference.

Accordingly, in a preferred embodiment, the invention relates to the marker gene of the first aspect, which is transcribed from at least one heterologous and/or artificial promoter.

Of course, an aspect of the invention relates to polynucleotide constructs comprising at least one recombinant marker gene of the first aspect.

Correspondingly, a preferred embodiment of the invention relates to the polynucleotide construct of the second aspect, wherein the at least one recombinant marker gene is a selection marker, a screening marker, a counter-selection marker, or a bi-directional selection marker.

Another preferred embodiment relates to the polynucleotide construct of the second aspect, wherein the encoded orotate transporter polypeptide also transports one or more orotate analogues; preferably the orotate analogue 5-fluoroorotate.

Yet another preferred embodiment relates to the polynucleotide construct of the second aspect, wherein the marker gene is transcribed from at least one heterologous and/or artificial promoter.

Several different kinds of polynucleotide constructs are known to the skilled person, best-known are probably RNA and DNA, and in a preferred embodiment, the polynucleotide construct of the second aspect is DNA.

When a polynucleotide is introduced into a host cell, it may be as an extrachromosomal entity, e.g., a plasmid, and it may remain as such in the cell, provided it is replicated along with the cell, and parsed into all progeny cells when the cell divides or buds during growth. Sequences have been identified, which when present on an extrachromosomal polynucleotide construct ensure the stability and maintenance of the construct in the cell, and they have been referred to as autonomous replication sequences (ARS) or autonomous maintenance sequences (AMA).

A preferred embodiment of the invention relates to the polynucleotide construct of the second aspect, wherein the construct is extrachromosomal and comprises one or more sequence(s) providing autonomous replication and/or autonomous maintenance in a host cell, preferably ARS, or AMA1.

In some cases a polynucleotide construct is integrated into the genome of the host cell, and this is also a preferred embodiment of the present invention.

Other preferred embodiments of the second aspect relate to the polynucleotide construct, which is a plasmid, a linearized plasmid, or a multimerized plasmid, and preferably the plasmid comprises at least one origin of replication that is functional in a host cell.

While it is desirable not to use antibiotic resistance encoding markers in industrial host cells, it may be advantageous to use them in intermediary host cell construction steps, only to remove them at a later stage.

Therefore, a preferred embodiment of the second aspect relates to the polynucleotide, which further comprises at least one selection marker gene which encodes a polypeptide, which in turn confers resistance to an antibiotic when expressed in a host cell.

A third aspect relates to a cell comprising at least one exogenous marker gene of the first aspect, or a polynucleotide construct of the second aspect.

Correspondingly, a preferred embodiment of the third aspect is the cell, wherein the at least one marker gene is a selection marker, a screening marker, a counter-selection marker, or a bi-directional selection marker. It is also preferred that the at least one marker gene encoded orotate transporter polypeptide also transports one or more orotate analogues, preferably 5-fluoroorotate.

Likewise, it is preferred that the at least one marker gene is transcribed from at least one heterologous and/or artificial promoter, as mentioned above.

The present invention is applicable in a wide variety of host cells, as outlined elsewhere herein. Non-limiting examples of the use of the invention in Gram-negative and Gram-positive bacterial cells, *Lactococcus, Bacillus*, and *Escherichia* are shown in the examples below.

However, it is preferred that the cell of third aspect is a microbial cell, preferably a bacterial cell, more preferably a Gram-negative or Gram-positive bacterial cell, and most preferably of the genus *Lactobacillus, Bacillus*, or *Escherichia*.

Generally, cells which have been screened or selected for the acquisition of the ysbC marker in a previous step, may subsequently be screened or selected for loss of the very same marker in a counter-selection protocol. A marker gene, which can be used for the stepwise introduction of a polynucleotide construct comprising the marker gene into a host cell, followed by the curing of the construct from the host cell, often leaving some part of the construct behind, is frequently referred to as a bi-directional marker gene.

One example is if the cells are auxotrophic for pyrimidines in the absence of the ysbC marker, then the loss of the marker will result in an inhibition of their growth, without externally supplied pyrimidines. This allows an easy screening setup, as outlined in the examples above.

Another example is if the cells are resistant to the inhibitory orotate analogue 5-fluoroorotate (FOA) in the absence of the ysbC marker, then the loss of the marker will result in the cells becoming resistant again. This allows an easy selection setup, as outlined in the examples above.

The final aspect of the invention relates to a method of selecting or identifying a cell comprising at least one copy of a recombinant marker gene, and/or selecting or identifying a cell which has been cured of the recombinant marker gene, wherein said marker gene encodes an orotate transporter polypeptide comprising an amino acid sequence at least 60% identical to SEQ ID NO: 2, said method comprising the step of using the marker gene as a selection marker, a screening marker, a counter-selection marker, or a bi-directional marker, under suitable conditions, whereby the cell is selected or identified.

A preferred embodiment of the invention relates to the method of the final aspect, wherein the cell is pyrimidine auxotrophic and lacks a functional orotate transporter protein in the absence of the recombinant marker, and wherein the recombinant marker is introduced into the auxotrophic host cell, which is then cultivated in a growth medium with no uracil but supplemented with orotate, wherein only the cell comprising the recombinant marker will grow, wherein the marker is used as a selection marker.

Another preferred embodiment relates to the method of the final aspect, wherein the cell is pyrimidine auxotrophic, and comprises the recombinant marker gene which encodes a functional orotate transporter protein, and wherein the marker gene is then cured from the cell, which is cultivated in a growth medium with no uracil, wherein only the cell cured of the marker gene is inhibited, wherein the marker is used as a screening marker; preferably the cell is pyrimidine auxotrophic due to a mutation in at least one gene encoding an enzyme which converts dihydro-orotate to orotate, and preferably due to a mutation in one or more of pyrD, pyrDa, pyrDb, and pyrK.

Yet another preferred embodiment relates to the method of the final aspect, wherein the cell lacks a functional orotate transporter protein in the absence of the recombinant marker, and is resistant to the orotate analogue 5-fluoroorotate, and wherein the recombinant marker is introduced into the cell, which is then cultivated in a growth medium supplemented with an inhibitory concentration of FOA, wherein only the cell comprising the recombinant marker is sensitive to FOA and is inhibited, wherein the marker is used as a screening marker.

Still another preferred embodiment relates to the method of the final aspect, wherein the cell comprises the recombinant marker gene and is sensitive to FOA, and wherein the marker gene is then cured from the cell, which is cultivated in a growth medium supplemented with an inhibitory concentration of FOA, wherein only the FOA-resistant cell cured of the recombinant marker gene will grow, wherein the marker is used as a counter-selection marker.

A preferred embodiment of the invention relates to the method of the final aspect, wherein the cell comprising at least one copy of the recombinant marker gene is first selected or identified, and subsequently a cell which has been cured of the recombinant marker gene is selected or identified, wherein the marker is used ans a bi-directional marker; preferably wherein the cell is resistant to FOA, pyrimidine auxotrophic, and lacks a functional orotate transporter protein in the absence of the recombinant marker, and wherein the recombinant marker is first introduced into the orotate auxotrophic host cell, which is then cultivated in a growth medium supplemented with orotate, wherein only the cell comprising the recombinant marker will grow, and subsequently the marker gene is then cured from the cell by cultivation in a growth medium supplemented with an inhibitory concentration of FOA, wherein only the FOA-resistant cell cured of the recombinant marker gene will grow, wherein the marker is used as a bi-directional selection marker; preferably the cell is pyrimidine auxotrophic due to a mutation in a gene encoding an enzyme which converts dihydro-orotate to orotate, preferably due to a mutation in one or more of pyrD, pyrDa, pyrDb, and pyrK.

EXAMPLES

The inventors anticipate that the orotate transporter of the present invention will be functional in a very broad spectrum of host cells, including both eukaryotic and prokaryotic cells. As non-limiting examples of the functionality of the orotate transporter, its use is demonstrated in three very different types of bacteria: *Lactococcus lactis* (*L. lactis*) in Example 1, *Escherichia coli* (*E. coli*) in Example 2, and *Bacillus subtilis* (*B. subtilis*) in Example 3.

Strains and Plasmids

Media and Growth Conditions

*L. lactis* Media

| SA-glucose medium (Jensen and Hammer, 1993) | |
|---|---|
| 100 ml | 10 × MOPS |
| 10 ml | Vitamin solution |
| 100 ml | 17 L-amino acid solution |
| 100 mg | L-cysteine (as powder) |

TABLE 1

Strains and Plasmids used in the examples.

| | Genotype description and characteristics[1] | Reference |
|---|---|---|
| Strains: | | |
| *Lactococcus lactis* ssp. *cremoris* | | |
| MG2363 | Plasmid-free strain | Gasson, 1983 |
| NCDO712 | | Gasson, 1983 |
| MG1363 | | Gasson, 1983 |
| ED58.82 | MG1363 ΔpyrDa | Example 1 |
| ED79.1175 | MG1363 ΔpyrDa ΔpyrDb (U$^-$) | Example 1 |
| *Escherichia coli* | | |
| DH5alpha | F'Φ80dlacZΔM15 Δ(lacZYA-argF)U169 deoR recA1 endA1 hsdR17 ($r_k^-$, $m_k^+$) phoA supE44 thi-1 gyrA96 relA1/F' proAB$^+$ lacI$^q$ZΔM15 Tn10(tet) | Laboratory strain |
| KUR1351 | araD139 ΔlacU169 rpsL thi ΔpyrB usp-4 out-2 | Baker et al., 1996 |
| XL1-Blue | endA1 hsdR17 ($r_{k12}^-$, $m_{k12}^+$) supE44 thi-1 recA1 gyrA96 relA1 lac F'[proAB lacI$^q$ZΔM15 tet] | Laboratory strain |
| *Bacillus subtilis* | | |
| HH263 | 168 trpC2 | Laboratory strain |
| HH180 | 168 trpC2 pyrB (U$^-$) | Potvin et al., 1975 |
| ED344 | HH263 amyE::pDG268 (Neo$^r$) | Example 3 |
| ED348 | HH263 amyE::pED301 (OR$^+$, Neo$^r$) | Example 3 |
| ED364 | HH180 amyE::pDG268 (Neo$^r$) | Example 3 |
| ED358 | HH180 amyE::pED307 (OR$^+$, Neo$^r$) | Example 3 |
| Plasmids: | | |
| pCR ® 2.1-TOPO ® | bla kan; *E. coli* vector | InVitrogen Inc. |
| pGhost$^+$4 | erm ori$^{Ts}$; *L. lactis* vector | Magiun et al., 1996 |
| pCI3440 | cam; *E. coli-L. lactis* shuttle vector | |
| pDG268 | bla neo; *B. subtilis* integration vector | C. W. Price |
| pDBORO | ysbC | Example 1 |
| pED102 | bla kan ΔpyrDa; *E. coli* vector | Example 1 |
| pED202 | bla kan erm pyrDa; fusion of *E. coli* vector and *L. lactis* vector | Example 1 |
| pED105 | bla kan ΔpyrDb; *E. coli* vector | Example 1 |
| pED204 | bla kan erm ΔpyrDb; fusion of *E. coli* vector and *L. lactis* vector | Example 1 |
| pED112 | bla kan ysbC ysbB ysbA; *E. coli* vector | Example 1 |
| pED210 | cam ysbC ysbB ysbA; *E. coli-L. lactis* shuttle vector | Example 1 |
| pED301 | bla neo ysbC, ysbB; *B. subtilis* integration vector | Example 2, 3 |
| pED307 | bla neo ysbC ysbB ysbA; *B. subtilis* integration vector | Example 3 |

[1]U$^-$: uracil requirement;
OR$^+$: orotate utilization;
Neo$^r$: neomycin resistance;
ysbC, ysbB and ysbA derived from plasmid pDBORO (unpublished results).

| SA-glucose medium (Jensen and Hammer, 1993) | |
|---|---|
| 50 mg | L-tyrosine (as powder) |
| 5 ml | 1.9M NH$_4$Cl |
| 1 ml | 0.276M K$_2$SO$_4$ |
| 10 ml | 0.132M K$_2$HPO$_4$ |
| 5 ml | 3M NaOAc pH 7.0 |
| 50 ml | 20% glucose solution |

For liquid medium, add autoclaved, distilled H$_2$O up to 1 liter and sterilize through an 0.2 micrometer filter. Before use, add any necessary auxotrophic requirements and antibiotics.

For agar plates, add autoclaved, distilled H$_2$O up to 500 ml and sterilize through an 0.2 micrometer filter. Add 15 g agar to 500 ml distilled H$_2$O, autoclave, cool to 55° C., mix with the sterilized 2×SA-glucose concentrate, add any necessary auxotrophic requirements and antibiotics, and pour the agar plates.

| 10 × MOPS | |
|---|---|
| 400 ml | 1M MOPS/KOH pH 7.4 (freshly made) |
| 40 ml | 1M Tricine/KOH pH 7.4 (freshly made) |
| 10 ml | 10 mM FeSO$_4$ |
| 10 ml | 0.5 mM CaCl$_2$ |
| 5.3 ml | 1M MgCl$_2$ |
| 100 ml | 5M NaCl |
| 10 ml | micronutrients |
| 425 ml | autoclaved, distilled H$_2$O |

Sterilize through an 0.2 micrometer filter, keep frozen.

| Micronutrients | |
|---|---|
| 3 micro-M | (Nh$_4$)$_6$(MO$_7$)$_{24}$ |
| 400 micro-M | H$_3$BO$_3$ |
| 30 micro-M | CoCl$_2$ |
| 10 micro-M | CuSO$_4$ |
| 80 micro-M | MnCl$_2$ |
| 10 micro-M | ZnSO$_4$ |

Sterilize through an 0.2 micrometer filter, keep frozen.

| 17 L-amino acid solution | |
|---|---|
| 3.0 g | each of L-Alanine, L-Glutamate, L-Proline, L-Serine |
| 2.0 g | each of L-Arginine, L-Glycine, L-Lysine, L-Phenylalanine, L-Threonine |
| 1.0 g | each of L-Asparagine, L-Glutamine, L-Isoleucine, L-Leucine, L-Methionine, L-Trypthophan, L-Valine |
| 0.5 g | L-Histidine |

Add autoclaved, distilled H$_2$O up to 1 liter, adjust to pH 7.0 and sterilize through an 0.2 micrometer filter, keep frozen.

| Vitamin solution | |
|---|---|
| 10 mg | Biotin |
| 100 mg | Folic acid |
| 100 mg | Riboflavin |
| 100 mg | Niacinamide |
| 100 mg | Thiamine |
| 100 mg | Calcium pantothenate |
| 200 mg | Pyridoxal |

Add autoclaved, distilled H$_2$O up to 1 liter, adjust to pH 7.0 and sterilize through an 0.2 micrometer filter, keep frozen.

| M17-glucose medium (Terzaghi and Sandine, 1975) | |
|---|---|
| 5.0 g | tryptone |
| 5.0 g | soya pepton |
| 5.0 g | meat-extract |
| 2.5 g | yeast extract |
| 0.5 g | ascorbic acid |
| 0.25 g | MgSO$_4$ |
| 19 g | Na$_2$-glycerophosphate |

For liquid medium, add H$_2$O up to 1 liter and autoclave. pH is around 6.9. Add 0.5% glucose and any necessary auxotrophic requirements and antibiotics before use.

For agar plates, add H$_2$O up to 1 liter and 15 g agar and autoclave. Cool down to 55° C., add 0.5% glucose and any necessary auxotrophic requirements and antibiotics, and pour the agar plates.

| SR medium for agar plates (Holo and Nes, 1989) | |
|---|---|
| 10 g | tryptone |
| 5 g | yeast extract |
| 100 g | sucrose |
| | Add H$_2$O up to 1 liter up and if necessary, adjust the pH to 6.8, then add |
| 25 g | gelatine |
| 15 g | agar |

Autoclave, cool down to 55° C., add any necessary auxotrophic requirements and antibiotics, and pour the agar plates.

*E. coli* Media

| LB medium | |
|---|---|
| 10 g | Pepton from casein, pancreatically digested |
| 5 g | Bacto-yeast extract |
| 4 g | NaCl |

For liquid medium, add H$_2$O up to 1 liter, adjust pH to 7.0 and autoclave. Before use, add evt. the necessary auxotrophic requirements and antibiotics.

For agar plates, add H$_2$O up to 1 liter, adjust pH to 7.0, add 15 g agar, autoclave, cool down to 55° C., add any necessary auxotrophic requirements and antibiotics, and pour the plates.

| ABTG medium (Clark and Maaløe, 1967) For 250 ml: | |
|---|---|
| 1 ml | A10 |
| 9 ml | BT (bacto) agar |
| 1% or 2% | 20% Casamino acids |
| 0.2% | glucose |

Cool ABTG medium down to 55° C., add any necessary auxotrophic requirements and antibiotics, and pour the agar plates.

| A10 (100 ml): | |
|---|---|
| 2 g | $(NH_4)_2SO_4$ |
| 6 g | $Na_2HPO_4$ |
| 3 g | $KH_2PO_4$ |
| 3 g | NaCl; Add 80 ml $H_2O$, adjust pH to 6.4 and $H_2O$ to 100 ml |
| | BT: |
| 3.75 g | Bacto-agar |
| 150 ml | $H_2O$; Autoclave |

*Bacillus subtilis* Media

| LB medium | |
|---|---|
| 10 g | Pepton from casein, pancreatically digested |
| 5 g | Bacto-yeast extract |
| 4 g | NaCl |

For liquid medium, add $H_2O$ up to 1 liter, adjust pH to 7.0 and autoclave. Before use, add evt. the necessary auxotrophic requirements and antibiotics.

For agar plates, add $H_2O$ up to 1 liter, adjust pH to 7.0, add 15 g agar, autoclave, cool down to 55° C., add any necessary auxotrophic requirements and antibiotics, and pour the plates.

| GM1 medium | |
|---|---|
| 85 ml | demineralized $H_2O$ |
| 10 ml | 10 × MM solution |
| 150 microliter | 1M $MgSO_4$ |
| 1.0 ml | yeast extract 5% |
| 1.0 ml | 1 mg/ml Thiamine (B1) |
| 250 microliter | 20% Casamino acids |
| 1.0 ml | 4 mg/ml Trypthophane solution |
| 2.5 ml | 20% glucose; Add any necessary auxotrophic requirements and antibiotics. |

| GM2 medium | |
|---|---|
| 85 ml | demineralized $H_2O$ |
| 10 ml | 10 × MM solution |
| 0.5 ml | 1M $MgSO_4$ |
| 0.5 ml | yeast extract 5% |
| 1.0 ml | 1 mg/ml Thiamine (B1) |
| 1.0 ml | 4 mg/ml Trypthophane solution |
| 2.5 ml | 20% glucose; Add any necessary auxothrophic requirements and antibiotics. |

| 10 × MM solution | |
|---|---|
| 20 g | $(NH_4)_2SO_4$ |
| 106 g | $K_2HPO_4 \cdot 3H_2O$ |
| 60 g | $KH_2PO_4$ |
| 10 g | Na-citrate$\cdot 2H_2O$ |
| 2 g | $MgSO_4 \cdot 7H_2O$; Add 700 ml MilliQ $H_2O$, adjust pH to 7.0 with 10N NaOH and add MilliQ $H_2O$ to 1 liter |

| Minimal medium (500 ml): | |
|---|---|
| 400 ml | demineralized $H_2O$ |
| 100 ml | 5 × SZ |
| 5 ml | 20% glutamate |
| 1 ml | 0.1 mg/ml $MnSO4$ |
| 250 microliter | 50 mM FeCl3 |
| 5 ml | 1 mg/ml Thiamine (B1) |
| 5 ml | 4 mg/ml Trypthophane solution |
| 10 ml | glucose 20%; Add any necessary auxotrophic requirements and antibiotics. |

| Minimal medium for agar plates (500 ml): | |
|---|---|
| 400 ml | demineralized $H_2O$ |
| 10 g | Bacto agar |
| | autoclave, cool down to 55° C. |
| Add: | |
| 100 ml | 5 × SZ |
| 5 ml | 20% glutamate |
| 1 ml | 0.1 mg/ml $MnSO4$ |
| 250 microliter | 50 mM FeCl3 |
| 5 ml | 1 mg/ml Thiamine (B1) |
| 5 ml | 4 mg/ml Trypthophane solution |
| 10 ml | glucose 20%; Add any necessary auxotrophic requirements and antibiotics, and pour the agar plates. |

| 5 × SZ (Spizizens salts) | |
|---|---|
| 10 g | $(NH_4)_2SO_4$ |
| 70 g | $K_2HPO_4 \cdot 3H_2O$ |
| 30 g | $KH_2PO_4$ |
| 5 g | Na-citrate$\cdot 2H_2O$ |
| 1 g | $MgSO_4 \cdot 7H_2O$; Add 700 ml MilliQ $H_2O$, adjust pH to 7.0 with 10N NaOH and add MilliQ $H_2O$ to 1 liter |

| 1% Starch agar plates (500 ml): | |
|---|---|
| 5.0 g | Pepton from casein, pancreatically digested |
| 2.5 g | Bacto-yeast extract |
| 2.0 g | NaCl |
| | Add $H_2O$ to 500 ml, adjust pH to 7.2 |
| 5.0 g | Soluble starch |
| 10 g | agar |

Autoclave, cool down to 55° C., add any necessary auxotrophic requirements and antibiotics, and pour the plates.

| Potassium iodide solution | |
|---|---|
| 0.5% | Iodide |
| 1.0% | Potassium iodide |

Growth Conditions

Lactococcal cultures were grown at 30° C. either in M17 broth (Terzaghi and Sandine, 1975) or in minimal SA-medium (Jensen and Hammer, 1993) supplemented with 0.5% and 1% glucose, respectively. *E. coli* strains were grown at 37° C. either in Luria-Bertani (LB) broth or in minimal ABTG medium (Clark and Maaløe, 1967). *B. subtilis* strains were grown at 37° C. either in LB medium or in minimal MM medium. Agar plates were made by adding 15 g/ml agar to the broth medium. If necessary, the following supplements were added to the different media: orotate at 20 micro-g/ml, uracil at 20 micro-g/ml, 5-fluoroorotate (FOA) at 20 micro-g/ml, erythromycin at 5 micro-g/ml, chloramphenicol at 5 micro-g/ml for lactococci and 20 micro-g/ml for *E. coli*, ampicillin at 100 micro-g/ml.

Transformation

Transformation of *L. lactis* was performed by electroporation according to Holo and Nes (1989). For the transformation of the total plasmid preparation into *L. lactic* ED79.1175, supplemented minimal medium (SA-glucose) agar plates containing SA-medium, 1% glucose, 250 mM sucrose, 2.5 micro-M $CaCl_2$, 2.5 micro-M $MgCl_2$ and 100 micro-g/ml orotate were used instead of the ones described in Holo and Nes (1989).

*E. coli* cells were transformed using the calcium chloride procedure (Mandel and Higa, 1970) and the heat shock procedure (Volckaert et al., 1984).

Transformation of *B. subtilis* cells was carried out in the following way (Boylan et al., 1972): competent *B. subtilis* cells were made by adding 3 ml of an overnight culture (not lysed) grown in GM1 medium to 10 ml fresh GM1 medium and incubation for 4½ h at 37° C. The bacterial culture was subsequently ¹/₁₀ diluted in GM2 medium and incubated for 1 h at 37° C. For HH180 cells, 20 micro-g/ml uracil was added to the GM1 and GM2 medium. For the transformation 1 ml of the competent culture was mixed with 10 or 30 micro-1 of the linearized plasmid solution and the mixture was incubated for 35 min at 37° C. Cells were centrifuged for 4 min and the cell pellet was resuspended in 200 micro-I 0.9% NaCl solution and plated on selective LB plates containing 5 micro-g/ml neomycine. The plates were incubated overnight at 37° C.

Molecular Cloning Techniques and Oligonucleotides

Chromosomal DNA from lactococci and *B. subtilis* was prepared as described by Johansen and Kibenich (1992). Plasmid DNA was obtained by purification on Qiagen anion-exchange columns according to protocols described of Qiagen. Standard molecular cloning techniques were used according to Sambrook et al. (1989). Restriction endonucleases are purchased from Fermentas, the shrimp alkaline phosphatase and the $T_4$ DNA ligase are both purchased from Roche. The Elongase® Enzyme mix is from Life Technologies, the AmpliTaq DNA polymerase from Perkin Elmer and the Cloned Pfu DNA polymerase and TaqPlus® Precision PCR system are from Stratagene. The TOPO TA Cloning® kit is purchased from Invitrogen Inc. The Gene Clean kit used for the purification of DNA fragments from an agarose gel is from BIO101 Inc.

The synthetic oligonucleotides used in the examples are listed in table 2. Oligonucleotides are purchased from TAG Copenhagen A/S.

TABLE 2

Synthetic oligonucleotides used in the examples.

| Primer | SEQ ID NO | Nucleotide sequence 5'→ |
|---|---|---|
| pyrDaBamHI | 3 | cgggatccatgaccgcaccaacagc |
| pyrDaNcoI | 4 | catgccatggccaaatccatcttta ggc |
| pyrDaHindIII | 5 | cgtgaagcttgacaaaataggctgac ctc |
| PSA17 | 6 | atgccgcctcatcatttgac |
| PSA20 | 7 | atatcatctcttttggtaat |
| pyrDbIF | 8 | cggaagatctgatgatgacagttgt cag |
| pyrDbIR | 9 | ctgtactggtccataagctcggatc caccaaaacaacctgacgctg |
| pyrDbIIF | 10 | cagcgtcaggttgttttggtggatc cgagcttatggaccagtacag |
| pyrDbIIR | 11 | tcggagatctatccaaggacaagt gcag |
| pyrDbseq1 | 12 | tggtggaattggggttc |
| pyrDbseq2 | 13 | caaggtctgcgaagatg |
| pyrDbseq3 | 14 | attgacagaactgccag |
| DBORO2 | 15 | acttatcgtccggacttg |
| DBORO8 | 16 | cattagaaagcgcacgac |
| DBORO22BamHI | 17 | caggatcctactgacagacttgt cag |
| DBORO23EcoRI | 18 | gagaattctgattcggacaaggc ttc |
| DBORO24EcoRI | 19 | gagaattcaaagtcgttcgcctc aag |
| DBORO4 | 20 | ttcacgctcactaccttc |
| DBORO20 | 21 | ggctcaccattttttggcctctgg |
| 268neo | 22 | ctcattccctgatctcg |

PCR Amplification of DNA

Amplification of DNA was performed on chromosomal or plasmid DNA in a final volume of 50 micro-I containing 200 micro-M of each deoxyribonucleoside triphosphate, 200 nM of each oligonucleotide, and Taq polymerase. AmpliTaq™ DNA polymerase (2.5 U) was used in the verification experiments. For cloning purposes Pfu DNA polymerase, TaqPlus® Precision polymerase mixture, or Elongase® was used according the manufacturer's recommendations. Amplification was mostly performed with 25-30 cycles of 50 sec at 95° C., of 50 sec at 50° C., and of 1-5 min at 72° C.

DNA Sequencing

DNA sequences were determined by the enzymatic dideoxynucleotide chain termination method (Sanger et al., 1977) using the Thermo Sequenase and 20 micro-Ci[alpha-$^{35}$S] dATP (both from Amersham Pharmacia Biotech). Double stranded alkali-denatured plasmid DNA was used as template DNA and synthetic oligonucleotides were used as primers.

Detection of Alpha-Amylase Activity in *B. subtilis*

Detection of the alpha-amylase activity in *B. subtilis* was performed by adding a solution of 0.5% iodine and 1% potassium iodine to colonies grown on LB agar plates containing 1% starch. The alpha-amylase producing colonies formed a clear halo, whereas the alpha-amylase negative colonies did not.

Example 1

Construction Outline for *L. lactis* ssp. *cremoris* Strain ED79.1175

The *L. lactis* ssp. *cremoris* strain ED79.1175 is a MG1363 ΔpyrDa ΔpyrDb mutant, harboring deletions in the pyrDa and pyrDb genes. These two deletions result in a pyrimidine-requirement of the strain, which can be bypassed by addition of uracil to the growth medium of the strain. The parent strain MG1363 (Gasson, 1983) is prototrophic for pyrimidines. Both pyrDa and pyrDb encode a functional dihydroorotate dehydrogenase that catalyzes the conversion of dihydroorotate into orotate, the fourth step in the de novo pyrimidine biosynthesis shown in FIG. 1 (Andersen et al., 1994, 1996). Both pyrDa and pyrDb open reading frames are 933 basepairs (bp) long, and their respective gene products comprise 311 amino acid (aa) residues each.

A DNA fragment of 261 bp was deleted in the C-terminal part of the pyrDa gene in MG1363 resulting in a truncated and incomplete ΔpyrDa gene product of only 224 aa residues. An internal DNA fragment of 780 bp was then deleted from the pyrDb leaving DNA coding for 28 N-terminal and 24 C-terminal amino acid residues of the original protein behind.

The pyrDa and pyrDb genes of MG1363 with deletions were cloned into the vector pCR®2.1-TOPO® (Invitrogen), and the resulting constructs were fused to the pGhost⁺4 vector (Maguin et al., 1993) to perform sequential gene replacements in *L. lactis* as described in detail below. The resulting MG1363 ΔpyrDa mutant was denoted ED58.82, and the MG1363 ΔpyrDa ΔpyrDb double-mutant was denoted ED79.1175.

Construction of Plasmids pRL101, pED102 and pED202

Plasmid pIP61 contains the complete pyrDa gene (Andersen et al., 1994). Plasmid pRL101 contains a deleted pyrDa of which a 261 bp DNA fragment was deleted in the C-terminal part of the pyrDa gene (between position 653 and 914) by a combination of PCR and BamHI-NcoI digestion. PCR was carried out on pIP61 plasmid DNA with primers pyrDa-BamHI (SEQ ID NO:3) and pyrDaNcoI (SEQ ID NO:4). Both pIP61 and the PCR product were digested with BamHI and NcoI, ligated together and transformed into the *Escherichia coli* host XL1-Blue at 37° C. with selection for 100 micro-g/ml ampicillin resulting in pRL101 (Larsen, 1997).

Plasmid pED102 contains the ΔpyrDa gene. The deletion gene was amplified by the TaqPlus® Precision PCR system with primers pyrDaBamHI (SEQ ID NO:3) and pyrDaHindIII (SEQ ID NO:5) and subcloned into the vector pCR®2.1-TOPO® (Invitrogen) as described before. Reamplification with TaqPlus® Precision resulted in one specific fragment of 2249 bp which was purified from an agarosegel prior to cloning. The DNA fragment cloned in pED102 contains 933 bp upstream and 1316 bp downstream of the deletion site, respectively, necessary for the gene replacement in MG1363 (Biswas et al., 1993). The DNA sequence of the complete cloned DNA fragment in pED102 was verified by DNA sequencing.

Plasmid pED202 was made by ligating pED102 and pGhost⁺4 together through the XbaI-site which is unique in both constructs. After transformation to the *E. coli* host XL1-Blue, selection for the fusion constructs was carried out at 37° C. on LB plates containing both 100 micro-g/ml ampicillin and 150 micro-g/ml erythromycin. Only cells containing the fusion construct can survive on these selective LB plates.

First Gene Replacement—pyrDa in the Wildtype Strain MG1363

QIAGEN™ purified plasmid DNA of pED202 was introduced into competent MG1363 cells by electroporation. Transformants carrying plasmid pED202 were selected and purified at 28° C. on M17-glucose (Terzaghi and Sandine, 1975) plates containing 5 micro-g/ml erythromycin. In order to select for integration into the chromosome, pED202 containing transformants were streaked on M17-glucose plates containing 5 micro-g/ml erythromycin and 1% NaCl and incubated overnight at 37° C. Colonies were restreaked on similar plates and incubated overnight at 37° C. In order to facilitate excision of the plasmid by recombination, colonies were streaked on M17-glucose plates without erythromycin and incubated overnight at 28° C. Colonies were restreaked on similar plates and incubated overnight at 28° C. Cells were cured from the plasmid by streaking them on M17-glucose plates containing 1% NaCl and incubating overnight at 37° C. Colonies were restreaked on M17-glucose plates containing 1% NaCl and incubated overnight at 37° C. Colonies were screened for erythromycin sensitivity by streaking them on M17-glucose plates with and without 5 micro-g/ml erythromycin and incubating overnight at 28° C. Screening for strains in which pyrDa was deleted was carried out by extracting chromosomal DNA and PCR with primers PSA17 and PSA20. Strain ED58.82 gave the expected PCR fragment for a deleted pyrDa. The strain ED58.82 is prototrophic for pyrimidines, so a second gene-replacement or deletion of pyrDb must be carried out to create a pyrimidin auxotrophic strain.

Construction of Plasmids pED105 and pED204

The deletion of an internal fragment of 780 bp in the pyrDb gene was carried out by SOE. The SOE fragment comprises 1993 bp made up from 1013 bp upstream and 980 bp downstream, respectively, of the deletion site.

In the first PCR, two PCR fragments, PCR1 and PCR2, were amplified in separate reactions with Pfu DNA polymerase and MG1363 chromosomal DNA as template. Primers used for PCR1 are pyrDbIF (SEQ ID NO:8) and pyrDbIR (SEQ ID NO:9). Primers used for PCR2 are pyrDbIIF (SEQ ID NO:10) and pyrDbIIR (SEQ ID NO:11). The PCR fragments were purified from an agarosegel. To splice the two PCR products, PCR1 and PCR2 were used as templates in the SOE reaction using TaqPlus® Precision and primers pyrDbIF (SEQ ID NO:8) and pyrDbIIR (SEQ ID NO:11). The resulting PCR fragment was purified from an agarosegel and cloned into the vector pCR®2.1-TOPO® (Invitrogen) as described before. The resulting plasmid was called pED105, and the DNA sequence of its complete cloned DNA fragment was verified by DNA sequencing.

Plasmid pED204 was then made by ligating pED105 and pGhost⁺4 together through the XbaI-site which is unique in both constructs. After transformation to the *E. coli* host XL1-Blue, selection for the fusion constructs was carried out at 37° C. on LB plates containing both 100 micro-g/ml ampicillin and 150 micro-g/ml erythromycin. Only cells containing the fusion construct can survive on these selective LB plates.

Second Gene Replacement—pyrDb in Strain ED58.82 (MG1363 ΔpyrDa)

QIAGEN™ purified plasmid DNA of pED105 was introduced into competent ED58.82 cells by electroporation. Transformants carrying plasmid pED105 were selected and purified at 28° C. on M17-glucose plates supplied with erythromycin at 5 micro-g/ml. In order to select for integration in the chromosome, pED105 containing transformants were streaked on M17-glucose plates containing 5 micro-g/ml erythromycin and 1% NaCl and incubated overnight at 37° C. Colonies were restreaked on similar plates and incubated overnight at 37° C. In order to facilitate excision of the plasmid by recombination, colonies were streaked on M17-glucose plates without erythromycin and incubated overnight at 28° C. Colonies were restreaked on similar plates and incubated overnight at 28° C. Cells were cured from the plasmid by streaking them on M17-glucose plates containing 1% NaCl and incubating overnight at 37° C. Colonies were restreaked on M17-glucose plates containing 1% NaCl and incubating overnight at 37° C. Colonies were screened for erythromycin sensitivity by streaking them on M17-glucose plates with and without 5 micro-g/ml erythromycin and incubating overnight at 28° C.

Among the erythromycin sensitive colonies, strains in which both pyrDa and pyrDb were deleted were found by streaking colonies on both SA-glucose plates (Jensen and Hammer, 1993) and SA-glucose plates containing uracil (20 micro-g/ml) as sole pyrimidine source. A strain with the right deletions is not able to synthesize pyrimidines de novo and can thereby not grow on SA-glucose plates.

Deletions in the respective genes were verified by extracting chromosomal DNA from pyrimidine-requiring strains and PCR with primers PSA17 (SEQ ID NO:6) and PSA20 (SEQ ID NO:7) and primers pyrDbseq1 (SEQ ID NO:12) and pyrDbseq3 (SEQ ID NO:14) for pyrDa and pyrDb, respectively. The resulting strain, which was denoted ED79.1175, is not able to grow on SA-glucose plates unless a pyrimidine source is added, and the strain harbors the correct deletions in its chromosome. Since the ED79.1175 strain carries deletions in the genes catalyzing the reduction of dihydroorotate to orotate, it can be used to analyze orotate utilization. In addition, the strain ED79.1175 is resistant towards the analogue FOA.

Cloning of the ysbC Gene—Construction of pED112 and pED210

The ysbC gene that is responsible for the transport of orotate into the cell encodes a protein of 307 amino acid residues. Prediction of the transmembrane helices in the deduced amino acid sequence of the ysbC gene product, using the TMHMM Server v. 2.0 software program, revealed an overall structure of a membrane protein consisting of nine transmembrane regions.

A genomic library was isolated with the QIAGEN™ protocol for the isolation of large BAC and PAC plasmid clones. Two microliters of the total plasmid preparation thus prepared were transferred by electrotransformation into the pyrimidine auxothropic ED79.1175 strain, using 100 micro-g/ml orotate as selective agent.

Plasmid selection based on orotate utilization in ED79.1175 depends on the complementation of the pyrimidine auxothrophy of the strain. Therefore the agar plates used for the transformation were defined medium (SA-glucose) plates supplemented with 100 micro-g/ml orotate as the sole pyrimidine source. After two days, more than 1000 transformant colonies were observed growing on the selective medium. No colonies appeared on supplemented SA-glucose plates without orotate indicating that the obtained transformants had acquired gene information coding for orotate utilization or uptake.

Thirty-six transformants were restreaked on SA-glucose medium containing 100, 50 and 20 micro-g/ml orotate, respectively. The transformants grew at wildtype growth rate on all orotate concentrations. The plasmid profile of five transformants was analyzed, and all of them harbored only one single plasmid, denoted pDBORO.

A DNA fragment containing the ysbC gene (3688 bp) between primer DBORO2 (SEQ ID NO:15) and primer DBORO8 (SEQ ID NO:16) was PCR amplified from template QIAGEN™ purified plasmid pDBORO using the ELONGASE™ polymerase. The resulting PCR fragment was cloned into the vector pCR®2.1-TOPO® (Invitrogen) using the TOPO TA Cloning® system, and recombinant plasmids were selected at 37° C. on LB plates containing 100 micro-g/ml ampicillin. For distinction of recombinant clones, 0.1 mM IPTG and 40 micro-g/ml 5-bromo-4-chloro-3-indolyl-β-D-galactopyranoside (X-Gal) were added to the plates. The resulting recombinant plasmid was denoted pED112.

The DNA fragment was subsequently cut out from the plasmid pED112 through an EcoRI-digestion, ligated into the unique EcoRI-site of pCI3440 (Hayes et al., 1990), and amplified in the E. coli host strain DH5alpha at 37° C. with selection for 20 micro-g/ml chloramphenicol resistance. The resulting plasmid was called pED210.

ysbC as a Selection Marker in L. lactis

This example demonstrates that orotate utilization of strain ED79.1175 is mediated by ysbC.

QIAGEN™ purified plasmid DNA of pED210 or pCI3440 (negative control) was introduced into competent ED79.1175 cells by electroporation and transformants harboring plasmid pED210 or pCI3440 were selected at 30° C. on SR plates supplemented with 5 micro-g/ml chloramphenicol (Holo and Nes, 1989).

Transformants harboring either pED210 or pCI3440 were screened for orotate utilization by streaking them on SA-glucose plates containing 5 micro-g/ml chloramphenicol in the absence or presence of either orotate or uracil at 20 micro-g/ml. Incubation was done overnight at 30° C.

The ED79.1175 strain containing the vector pCI3440 (control) is only able to grow on SA-glucose medium supplemented with 20 micro-g/ml uracil. However, the ED79.1175 strain containing pED210 had gained the property to use orotate as the sole pyrimidine source due to the presence in the cell of the ysbC gene product from pED210, and this strain was able to grow on both plates.

The presence of the ysbC gene in only the orotate-utilizing strain, which harbours pED210, was verified by extracting DNA from both strains and performing a restriction endonuclease digestion with EcoRI. Only the strain which had pED210 produced a ysbC containing DNA restriction fragment.

This result demonstrates, that ysbC is suitable as a selection marker in cells that are normally auxotrophic for pyrimidines, i.e. orotate, wherein it indicates that those cells, which have become prototrophic, have acquired the desired polynucleotide construct comprising the ysbC marker.

ysbC as a Screening Marker in L. lactis

This example demonstrates that sensitivity towards the orotate analogue 5-fluoroorotate (FOA) of strains NCDO712 and MG1363 is mediated by ysbC.

The strains L. lactis NCDO712 (Gasson, 1983) and MG1363 (Gasson, 1983) are both L. lactis ssp. cremoris strains that are prototrophic for pyrimidines, and resistant to FOA.

QIAGEN™ purified plasmid DNA of pED210 and pCI3440 was introduced into competent NCDO712 and MG1363 cells by electroporation, and transformants harboring either plasmid pED210 or pCI3440 were selected at 30° C. on SR plates supplemented with 5 micro-g/ml chloramphenicol. Transformants harboring either pED210 or pCI3440 were screened for FOA sensitivity by streaking them on SA-glucose plates with 20 micro-g/ml FOA, and incubation overnight at 30° C.

The strains containing the vector pCI3440 (control) are resistant to FOA, while those containing the plasmid pED210, which comprises the ysbC-gene, had become FOA sensitive.

To verify that the FOA sensitivity was due to the presence of plasmid pED210, plasmid DNA was extracted from the FOA sensitive and insensitive strains, and then cleaved with restriction endonucleases EcoRI, as described above. Only the DNA isolated from the FOA sensitive strains gave rise to the restriction fragment with ysbC from pED210.

This result demonstrates that ysbC is suitable as a screening marker in cells normally resistant to FOA, wherein it indicates that those cells, which have become sensitive to FOA, have acquired the desired polynucleotide construct comprising the ysbC marker.

An ysbC gene was previously predicted in the genome-sequencing of a *L. lactis* strain, but its function was not established. Based on the experiments described above we have concluded, that ysbC most likely encodes an orotate transporter protein.

Example 2 pED301—Cloning of the ysbC Gene in the Vector pDG268

The vector pDG268 (C. W. Price) is an integrative vector for *Bacillus subtilis* that specifically integrates into the chromosomal amyE gene by a double cross-over recombination through the amyE N-terminal, and amyE C-terminal parts, located on pDG268. The plasmid also contains an *E. coli* origin, neomycin and ampicillin resistance markers, and the LacZ operon for blue/white distinction of recombinant clones in *Escherichia coli*. The cloning sites used for the molecular cloning of the ysbC gene are BamHI and EcoRI located in the N-terminal end of LacZ. The KpnI site is used for linearization in order to augment chromosomal integration.

A DNA fragment containing the ysbC gene (2048 bp) between primer DBORO22BamHI (SEQ ID NO:17) and primer DBORO23EcoRI (SEQ ID NO:18) was PCR amplified using ELONGASE™ polymerase, and QIAGEN™-purified plasmid DNA of plasmid pDBORO. The PCR fragment was cleaved by BamHI and EcoRI and ligated into the vector pDG268 (C. W. Price).

The resulting recombinant plasmid, denoted pED301, was amplified in the *E. coli* host strains XL1-blue and KUR1351 (Baker et al., 1996) at 37° C. on LB plates containing 100 micro-g/ml ampicillin.

ysbC as a Selection Marker in *E. coli* Strain KUR1351

Orotate utilization was investigated with plasmid pED112 (ysbC) and plasmid pED301 (ysbC). The parent plasmids pCR®2.1-TOPO® and pDG268 were used as negative controls, respectively.

QIAGEN™-purified plasmid DNA of the recombinant plasmid or the vector was introduced into competent *Escherichia coli* KUR1351 cells by the heat shock procedure (Mandel and Higa, 1970). Transformants containing plasmid DNA were selected at 37° C. on LB plates supplemented with 100 micro-g/ml ampicillin. The transformants were further screened for orotate utilization by streaking them on ABTG plates (Clark and Maaløe, 1967) in the absence and presence of either 20 micro-g/ml orotate, or 20 micro-g/ml uracil, as pyrimidine source.

To verify whether the orotate utilization was due to the presence of plasmid pED112 or pED301 in the cell, plasmid DNA was extracted from the orotate utilizing and non-utilizing strains, and cleaved with restriction endonuclease EcoRI (cutting out the 3688 bp DNA fragment containing ysbC) and BamHI-EcoRI (cutting out the 2048 bp DNA fragment containing ysbC), respectively. The results demonstrated, that the *L. lactis* orotate transporter, encoded by the ysbC gene present on a multi-copy episomal plasmid, is required for the transport of orotate into the Gram-negative bacterium *E. coli*, and that the imported orotate can satisfy the pyrimidine requirement of the *E. coli* KUR1351 strain. Furthermore, the functionality of the ysbC gene product is independent of the background vector.

ysbC as a Screening Marker in *E. coli* XL1-Blue

*E. coli* XL1-Blue is a commonly used laboratory strain that is prototrophic for pyrimidines and resistant to FOA.

QIAGEN™-purified plasmid DNA of pED301 (ysbC), or pDG268 (negative control) was introduced into competent XL1-Blue cells by the heat shock procedure, and transformants harboring plasmid pED301 or pDG268 were selected at 37° C. on LB plates supplemented with 100 micro-g/ml ampicillin. Transformants were screened for fluoroorotate sensitivity by streaking them on ABTG plates without or with 20 micro-g/ml fluoroorotate and incubation overnight at 37° C.

To verify if the FOA-sensitivity was due to the presence of plasmid pED301, plasmid DNA was extracted from the FOA sensitive and insensitive strains and cleaved with restriction endonuclease BamHI and EcoRI (cutting out the 2048 bp DNA fragment containing ysbC). Only the digests from the FOA sensitive strains had the distinct fragment indicating the presence of ysbC. It was concluded, that the *L. lactis* orotate transporter encoded by ysbC is also responsible for the FOA sensitivity of the *E. coli* XL1-Blue cells.

Example 3

Construction of Plasmid pED307 (ysbC)

The recombinant plasmid pED307 is constructed like pED301 (see example 2), except that primer DBORO24EcoRI (SEQ ID NO:19) was used as downstream primer instead of primer DBORO23EcoRI (SEQ ID NO:18), resulting in the amplification of a longer ysbC PCR fragment of 2693 bp.

ysbC as a Selection Marker in *Bacillus subtilis*

*Bacillus subtilis* HH180 is a 168 pyrB strain (Potvin et al., 1975) with a pyrimidine-requirement.

QIAGEN™-purified plasmid DNA of pED307 (ysbC) was linearized by cleavage with KpnI. Transformation of HH180 cells with linear pED307/KpnI was carried out exactly as described in materials and methods. To satisfy the pyrimidine requirement of the HH180 cells, 20 micro-g/ml uracil was added to the GM1 and GM2 medium.

Homologous recombination of pED307 by a double cross-over event into the amyE gene of HH180 was verified by streaking the transformants on 1% starch plates. The plates were incubated at 37° C. and the following day, 2 ml of a potassium iodide solution was spread over the surface of the plates. Transformants that produced a functional alpha-amylase, encoded by amyE, degraded the starch in the plates, and a clear halo was observed around the colonies after the iodide staining. Transformants with an integrated pED307 copy into the amyE gene remained purple showing no haloes.

Verification was also carried out at the DNA level. Chromosomal DNA was isolated from transformants with an integrated pED307 (ysbC) or pDG268 (negative control), and PCR amplifications were performed with primer set 268neo (SEQ ID NO:22) and DBORO20 (SEQ ID NO:21), and primer set 268neo (SEQ ID NO:22) and DBORO4 (SEQ ID NO:20), resulting in a PCR fragment of about 2070 bp and 1200 bp, respectively (data not shown). The strains ED364

(HH180 amyE::pDG268; control) and ED358 (HH180 amyE::pED307) were selected for screening for orotate utilization.

The strains ED364 (ysbC) and ED358 (control) were streaked on selective MM plates containing 5 micro-g/ml neomycine in the absence or presence of either 20 micro-g/ml orotate, or 20 micro-g/ml uracil, as sole pyrimidine source. The screening plates were incubated overnight at 37° C.

The results demonstrated that the *L. lactis* orotate transporter, encoded by ysbC, which was present as a single gene copy in the chromosome of the integrants, was able to transport orotate into the Gram-positive bacterium *B. subtilis*, and the imported orotate could satisfy the pyrimidine requirement of the HH180 strain.

ysbC as a Screening Marker in *B. subtilis*

*B. subtilis* HH263 is an FOA resistant laboratory strain 168 (trpC2) purchased from the 'Institut National de la Recherche Agronomique' (INRA), France.

QIAGEN™-purified plasmid DNA of pED301 (ysbC) was linearized by cleavage with KpnI, and transformation of HH263 cells with linear pED301/KpnI was carried out exactly as described in materials and methods. Verification of the integration of a copy of the pED301 plasmid into the chromosome was done on 1% starch plates, and at the DNA level, exactly as described above. The PCR amplifications resulted in a PCR fragment of about 1425 bp and 560 bp for primer set 268neo (SEQ ID NO:22) and DBORO20 (SEQ ID NO:21), and primer set 268neo (SEQ ID NO:22) and DBORO4 (SEQ ID NO:20), respectively (data not shown).

The resulting strains were denoted ED344 (HH263 amyE::pDG268) and ED348 (HH263 amyE::pED301). ED344 and ED348 were streaked on selective MM plates containing 5 micro-g/ml neomycine, one with 20 micro-g/ml FOA, and one without. The screening plates were incubated overnight at 37° C.

The results demonstrated ED344 was resistant to FOA, while ED348 was FOA sensitive, so the *L. lactis* orotate transporter encoded by ysbC was also able to mediate the transport of FOA into the Gram-positive bacterium *B. subtilis*. The conferred FOA sensitivity shows that the ysbC gene is responsible for the uptake of 5-fluoroorotate in *B. subtilis* cells.

REFERENCES

Andersen, P. S., Gildsig Jansen, P. J. and Hammer, K. (1994). Two different dihydroorotate dehydrogenases in *Lactococcus lactis*. *J. Bacteriol.* 176, 3975-3982.

Andersen, P. S., Martinussen, J. and K. Hammer, K. (1996). Sequence analysis and identification of the pyrKDbF operon from *Lactococcus lactis* including a novel gene, pyrK, involved in pyrimidine biosynthesis. *J. Bacteriol.* 178, 5005-5012.

Baker, K. E., Ditullio, K. P., Neuhard, J. and Kelln, R. A. (1996). Utilization of orotate as a pyrimidine source by *Salmonella typhimurium* and *Escherichia coli* requires the dicarboxylate transport protein encoded by dctA. *J. Bacteriol.* 178, 7099-7105.

Biswas, I., Gruss, A., Erhlich, S. D. and Maguin, E. (1993). High-efficiency gene inactivation and replacement system for gram-positive bacteria. *J. Bacteriol.* 175, 3628-3635.

Boylan, R. J., Mendelson, N. H., Brooks, D. and Young, F. E. (1972). Regulation of the bacterial cell wall. Analysis of a mutant of *Bacillus subtilis* defective in biosynthesis of techoic acid. *J. Bacteriol.* 110, 281-290.

Clark, D. J. and Maaløe, O. (1967). DNA replication and the cell cycle in *Escherichia coli*. *J. Mol. Biol.* 23, 99-112.

Gasson, M. J. (1983). Plasmid complements of *Streptococcus lactis* NCDO 712 and other streptococci after protoplast-induced curing. *J. Bacteriol.* 154, 1-9.

Grimberg, J., Maguire, S, and Belluscio, L. (1989). A simple method for the preparation of plasmid and chromosomal *E. coli* DNA. Nucleic Acids Res. 17, 8893.

Hayes, F., Daly, C. and Fitzgerald, G. F. (1990). Identification of the minimal replicon of *Lactococcus lactis* subsp. *lactis* UC317 plasmid pCI305. *Appl. Environ. Microbiol.* 56, 202-209.

Holo, H. and Nes, I, F. (1989). High-frequency transformation, by electroporation, of *Lactococcus lactis* subsp. *cremoris* grown with glycine in osmotically stabilized media. *Appl. Environ. Microbiol.* 55, 3119-3123.

Horton, R. M., Ho, S. N., Pullen, J. K., Hunt, H. D., Cai, Z., Pease, L. R. (1993). Gene splicing by overlap extension. *Methods Enzymol.* 217, 270-279.

Johansen, E. and Kibenich, A. (1992). Characterisation of *Leuconostoc* isolates from commercial mixed strain mesophilic starter cultures. *J. Dairy Sci.* 75, 1186-1191.

Jensen, P. R. and Hammer, K. (1993). Minimal requirements for exponential growth of *Lactococcus lactis*. *Appl. Environ. Microbiol.* 59, 4363-4366.

Larsen, R. (1997). Integration of deletions-mutation i pyrDa genet i *Lactococcus lactis* subsp. *cremoris*, MG1363. Project-rapport c920822.

Mandel, M. and Higa, A. (1970). Calcium-dependent bacteriophage DNA infection. *J. Mol. Biol.* 53, 154-162.

Potvin, B. W., Kelleher, R. J. Jr, and Gooder, H. (1975). Pyrimidine biosynthetic pathway of *Bacillus subtilis*. *J. Bacteriol.* 123, 604-615.

Sanger F. S. N. and Coulson, A. R. (1977). DNA sequencing with chain terminating inhibitors. *Proc. Natl. Acad. Sci. USA* 74, 5463-5467.

Terzaghi, B. E. and Sandine, W. E. (1975). Improved medium for lactic streptococci and their bacteriophages. *Appl. Microbiol.* 29, 807-813.

Volckaert, G., De Vleeschouwer, E., Blöcker, H. and Frank, R. (1984). A novel type of vectors for ultrarapid chemical degradation sequencing of DNA. *Genet. Anal.* 1, 52-59.

The invention claimed is:

1. A method of identifying a cell comprising at least one copy of a recombinant marker gene encoding an orotate transporter polypeptide comprising the steps of culturing the cell under suitable conditions; and identifying the cell with the marker gene, wherein said marker gene encodes an orotate transporter polypeptide comprising the amino acid sequence of SEQ ID NO: 2.

2. The method of claim 1, wherein the cell is pyrimidine auxotrophic and lacks a functional orotate transporter protein in the absence of the recombinant marker gene.

3. The method of claim 1, wherein the cell is pyrimidine auxotrophic and comprises the recombinant marker gene which encodes a functional orotate transporter protein.

4. The method of claim 1, wherein the cell is pyrimidine auxotrophic due to a mutation in at least one gene encoding an enzyme which converts dihydro-orotate to orotate.

5. The method of claim 4, wherein the cell is pyrimidine auxotrophic due to a mutation in one or more genes encoding dihydroorotate dehydrogenase, dihydroorotate dehydrogenase A, dihydroorotate dehydrogenase B or dihydroorotate dehydrogenase B electron transfer subunit.

6. The method of claim 1, comprising the step of cultivating the cell in a growth medium supplemented with an inhibitory concentration of 5-fluoroorotate.

7. The method of claim 1, wherein the cell comprises the recombinant marker gene and is sensitive to 5-fluoroorotate (FOA), and wherein the marker gene is then cured from the cell, which is cultivated in a growth medium supplemented with an inhibitory concentration of FOA, wherein only the FOA-resistant cell cured of the recombinant marker gene will grow, wherein the marker is used as a counter-selection marker.

8. The method of claim 1, wherein the marker is a bi-directional marker.

9. The method of claim 8, wherein the cell is resistant to 5-fluoroorotate (FOA), pyrimidine auxotrophic, and lacks a functional orotate transporter protein in the absence of the recombinant marker.

10. The method of claim 9, wherein the cell is pyrimidine auxotrophic due to a mutation in at least one gene encoding an enzyme which converts dihydro-orotate to orotate.

11. The method of claim 9, wherein the cell is pyrimidine auxotrophic due to a mutation in one or more genes encoding dihydroorotate dehydrogenase, dihydroorotate dehydrogenase A, dihydroorotate dehydrogenase B or dihydroorotate dehydrogenase B electron transfer subunit.

12. The method of claim 1, wherein said marker gene encodes an orotate transporter polypeptide consisting of the amino acid sequence of SEQ ID NO: 2.

13. The method of claim 12, wherein the cell is pyrimidine auxotrophic and lacks a functional orotate transporter protein in the absence of the recombinant marker gene.

14. The method of claim 12, wherein the cell is pyrimidine auxotrophic and comprises the recombinant marker gene which encodes a functional orotate transporter protein.

15. The method of claim 12, wherein the cell is pyrimidine auxotrophic due to a mutation in at least one gene encoding an enzyme which converts dihydro-orotate to orotate.

16. The method of claim 15, wherein the cell is pyrimidine auxotrophic due to a mutation in one or more genes encoding dihydroorotate dehydrogenase, dihydroorotate dehydrogenase A, dihydroorotate dehydrogenase B or dihydroorotate dehydrogenase B electron transfer subunit.

17. The method of claim 12, comprising the step of cultivating the cell in a growth medium supplemented with an inhibitory concentration of 5-fluoroorotate.

18. The method of claim 12, wherein the cell comprises the recombinant marker gene and is sensitive to 5-fluoroorotate (FOA), and wherein the marker gene is then cured from the cell, which is cultivated in a growth medium supplemented with an inhibitory concentration of FOA, wherein only the FOA-resistant cell cured of the recombinant marker gene will grow, wherein the marker is used as a counter-selection marker.

19. The method of claim 12, wherein the marker is a bi-directional marker.

20. The method of claim 19, wherein the cell is resistant to 5-fluoroorotate (FOA), pyrimidine auxotrophic, and lacks a functional orotate transporter protein in the absence of the recombinant marker.

21. The method of claim 20, wherein the cell is pyrimidine auxotrophic due to a mutation in at least one gene encoding an enzyme which converts dihydro-orotate to orotate.

22. The method of claim 20, wherein the cell is pyrimidine auxotrophic due to a mutation in one or more genes encoding dihydroorotate dehydrogenase, dihydroorotate dehydrogenase A, dihydroorotate dehydrogenase B or dihydroorotate dehydrogenase B electron transfer subunit.

* * * * *